United States Patent [19]

Pfleiderer et al.

[11] 4,012,285
[45] Mar. 15, 1977

[54] ANALYSIS OF ISOENZYME PATTERNS

[75] Inventors: Gerhard Pfleiderer, Witten; Hermann Lang, Darmstadt; Norbert Hennrich, Darmstadt; Hans Dieter Orth, Darmstadt, all of Germany

[73] Assignee: Merck Patent Gesellschaft mit beschrankter Haftung, Darmstadt, Germany

[22] Filed: Nov. 27, 1973

[21] Appl. No.: 419,283

[30] Foreign Application Priority Data

Dec. 1, 1972 Germany .................... 2258822

[52] U.S. Cl. .................... 195/103.5 R; 195/63; 424/2; 424/12
[51] Int. Cl.$^2$ .................... C12K 1/04; G01N 31/14
[58] Field of Search ................... 195/103.5

[56] References Cited

UNITED STATES PATENTS

| | | | |
|---|---|---|---|
| 3,817,837 | 6/1974 | Rubenstein et al. | 195/103.5 R |
| 3,932,221 | 1/1976 | Pfleiderer | 195/103.5 R |

OTHER PUBLICATIONS

Markert et al., Immunochemical Properties of Lactate Dehydrogenase Isoenzymes, Annals New York Academy of Sciences, 103, 1963 (pp. 915–929).
Van Loon et al., "Photometric Method for Blood Amylase by Use of Starch-Iodine Color," Am. J. Clin. Pathol. 22:1134 (1952).
McGeachin et al., "Serological Differentiation of Amylase Isozymes," Ann. N.Y. Acad. Sci., 94, pp. 996–1003 (1961).
Assicot et al., "Production of Antibodies to Catechol–O–Methyl–Transferase (EC2.1.1.6) of Rat Liver," Biochem. Pharmacology 18, pp. 1893–1898, (1969).
J.S. Nisselbaum et al., "Reactions of Lactic Dehydrogenase From Various Rabbit Organs With Antirabbit Muscle Lactic Dehydrogenase," J. of Biol. Chem., vol. 234 (12) pp. 3276–3280 (1959).
McGeachin et al., "Serological Differentiation of Amylase Isozymes," Ann. N.Y. Acad. Sci., 94, pp. 996–1003 (1961).

*Primary Examiner*—David M. Naff
*Assistant Examiner*—C. A. Fan
*Attorney, Agent, or Firm*—Millen & White

[57] ABSTRACT

Isoenzyme patterns of an enzyme in biological fluids, extracts, and/or excretions are quantitatively determined by precipitating at least 90% of an isoenzyme antigen with a corresponding heterologous antiserum and comparing the remaining enzyme activity with the total activity with the use of a conventional agent for enzyme activity determination.

12 Claims, No Drawings

ANALYSIS OF ISOENZYME PATTERNS

BACKGROUND OF THE INVENTION

This invention relates to a process for the analysis of the isoenzyme pattern of an enzyme in biological fluids, extracts or excretions.

Isoenzymes are molecular variants of the same enzyme which differs in molecular structure generally by only a few amino acid groups. Since the relative distribution of isoenzymes differs in different organs and since, like ordinary enzymes, isoenzymes are released into the bloodstream or other body fluids when an organ is diseased or damaged, the identity of the isoenzymes which appear is indicative of the organ from which they originate. For example, the enzyme lactic dehydrogenase occurs in at least five isoenzyme forms which are characteristically found in varying amounts in different organs; the isoenzyme patterns can be employed to diagnose over a dozen abnormal conditions, e.g., heart attacks and liver diseases. Similarly, creatine phosphokinase isoenzyme patterns can be used to detect minor heart damage undetectable by electrocardiograms.

Because all of the isoenzyme forms of a particular enzyme are structurally very similar, highly specific electrophoretic or immunological methods are required to identify and quantify individual isoenzyme forms.

German Patent Application No. P 21 28 670.4, corresponding to copending, commonly assigned U.S. patent application Ser. No. 261,215, filed June 9, 1972, now U.S. Pat. No. 3,932,221, the contents of which are incorporated by reference herein, describes an immunological test using practically completely precipitating antisera, obtained by means of pure human isoenzyme antigens (homologous antisera), to conduct an organ-, tissue- and/or disease-specific analysis of the isoenzyme pattern of an enzyme occurring in multiple molecular forms in human body fluids, extracts or excretions.

The isoenzyme test described therein has a number of advantages; in principle the activities of the individual isoenzymes of an eneyzme occurring in multiple molecular forms can be specifically determined in a quantitative manner. Due to the simplicity of the process, it has become possible to detect the entire isoenzyme patterns of diagnostically interesting enzymes without great expenditues in time and material by means of a routine analysis. Another advantage of this process is the precision of the method, surpassing frequently the accuracy of the heretofore employed isoenzyme determination methods, e.g., the various electrophoretic methods. At the same time, this process frequently makes it possible at all for the first time to clearly differentiate between the individual isoenzyme and/or hybrids.

Because of the breadth of possibilities of application and due to the simplicity with which it can be carried out, the method provides flawless differentiation of the isoenzyme pattern of an enzyme occurring in multiple molecular forms, so that indications can be made of the organ specificity and, if the isoenzymes of a certain enzyme are distributed in the cell among various cellular compartments, also of the intracellular distribution. Such analyses have heretofore been impractical due to the technical expenditures, complexity, and inaccuracy of earlier known methods.

The aforementioned isoenzyme test, however, also entails certain difficulties, primarily connected with the fact that the isoenzyme antigen required to produce the necessary antisera must first be isolated for human body parts. This causes severe problems for the antisera manufacturer on an ethical and also on a practical level.

Since the antigens employed for the production of the required antisera stem from human biological materials, the antisera manufacturer must work up autopsy material. Although heterologous antisera can also be obtained from animals, the use of human antigens for the manufacture thereof nonetheless represents a serious burden. Additionally, the working up of cadaver materials in order to obtain the antigen is problematical for the persons executing this task. Objectively, there is also the danger of infection, especially with infectious hepatitis, when working up the human liver.

Further practical difficulties arise because autopsy material can normally be taken only after a certain period of time, e.g. 18 hours after death. During this time, sensitive organs and/or tissues, e.g., the brain, are already subjected to autolysis. Therefore, it is extremely difficult to obtain pure isoenzyme-antigen preparations.

Faced with these difficulties, the question arose whether or not it would be possible to employ animal tissue matter for the isolation of the required isoenzyme antigons. However, the following prejudices exist against this procedure:

The precipitin reaction is known to be extremely specific. Even minute changes in the structure of an antigen can lead to the production of an antiserum resulting in reduced precipitation with the unchanged antigen, or even no precipitation at all. It is also known that analogous human and animal isoenzymes differ from one another to various degrees with respect to their structures.

Taking these facts into account, and in view of the consideration that, for the described isoenzyme test, a practically quantitatively removal of one or more isoenzyme antigens and thus maximum specificity of the antisera employed are required, it could be foreseen that the results attainable with heterologous antisera against animal antigens would not satisfy the specificity requirements given by the use of homologous antisera as the standard.

OBJECTS OF THE INVENTION

Accordingly, it is a general object of the present invention to provide a process and test kit for quantitatively precipitating isoenzymes with antisera to corresponding isoenzymes of a heterologous species.

Another object of this invention is to provide a process for obtaining a practically quantitative cross-reaction of immunoprecipitating antibodies to heterologous isoenzymes.

A further object of this invention is to provide a method for the detection of isoenzymes normally only with difficulties available from human organs to permit the preparation of antisera thereto.

A more particular object of this invention is to provide diagnostic methods and test kits for the detection of individual isoenzymes of aldolase, creatine kinase, lactate dehydrogenase, alkaline phosphatase, acidic phosphatase, γ-glutamyl transpeptidase, glutamate oxalacetate transaminase, glutamate pyruvate transaminase, hexokinase and amylase.

Yet another object of this invention is to provide diagnostic methods and test kits for the detection of hybrid isoenzymes.

An object of this invention is as well to provide a method indicating if the isoenzyme pattern in a biological fluid, extract or excretion is differing from the normal values of said isoenzyme pattern.

Other objects and advantages of this invention will become apparent upon further study of the specification and appended claims.

SUMMARY OF THE INVENTION

Briefly, the above and other objects are attained in one aspect of this invention by providing, in a diagnostic process for analyzing isoenzyme patterns in a species liquid sample of a biological fluid, extract or excretion which comprises determining the total enzymatic activity of an isoenzyme group in said liquid sample, precipitating at least one isoenzyme antigen of said isoenzyme group from said liquid sample with a corresponding isoenzymespecific immunoprecipitating antiserum, separating said precipitate, determining total residual enzymatic activity of said isoenzyme group in the resultant supernatant and comparing the enzymatic activities thereby determined, the improvement which comprises:

precipitating at least 90% of each of the relevant isoenzyme antigens of said isoenzyme group with the aid of one- to tenfold excess, based on the amount of antisera to the homologous isoenzyme antigens required to precipitate at least 90% of said isoenzyme antigens, of immunoprecipitating antisera to a corresponding isoenzyme group of a heterologous species, whereby substantially quantitative recovery of said isoenzyme group is obtained.

DETAILED DISCUSSION

It has now been found that it is possible, in some cases, to utilize animal antigens for producing the necessary antisera. A prerequisite therefor is that the antisera prepared against animal isoenzyme antigens result in practically quantitative precipitations with the heterologous human isoenzymes (and/or can be brought to a practically quantitative precipitation by suitable auxiliary agents), and that the antiserum excess required in the heterologous system for obtaining a practically quantitative precipitation is maintained within the theoretical limits given by the Heidelberger curve.

The newly discovered isoenzyme test has the same advantages over the prior art as mentioned above for the isoenzyme test described in the referenced copending U.S. Patent Application.

Moreover, the advantages afforded by changing from human antigens to animal antigens are, however, considerable. The ethical and health difficulties indicated above are eliminated. The danger of infection, which must be taken extremely seriously and which can only be reduced to a tolerable degree by a rather great technical expenditure involving the use of specific, germ-free rooms, changing clothing after each work step, availability of showers, disinfectants, etc. can be decreased. The problem of autolysis plays an insignificant role, with the possibility of working up the animal matter immediately after death.

Accordingly, the present invention relates to a process for analyzing the isoenzyme pattern of an enzyme in biological fluids, extracts and/or excretions by precipitating the isoenzyme antigens with corresponding antisera and by comparing the remaining enzyme activity with the total activity, with the use of a conventional agent for activity determination, which process is characterized in that the diagnostically relevant isoenzymes of the isoenzyme pattern are respectively precipitated with a one- to tenfold excess, as compared to the homologous antiserum, of a heterologous antiserum optionally with the use of auxiliary precipitants, which results in an at least 90% precipitation with the isoenzyme antigen to be determined.

The present invention furthermore relates to an agent for analyzing the isoenzyme pattern of an enzyme in body fluids, extracts and/or excretions, containing a test set of heterologous antisera, which are directed against the relevant isoenzymes of the isoenzyme pattern to be tested, are in each case precipitable to at least 90% with the isoenzyme antigens to be determined, optionally with the use of auxiliary precipitants, and yield with a one- to ten-fold excess based on the homologous antiserum, a practically quantitative cross-reaction, and further containing a conventional agent for the determination of enzyme activity.

Finally, this invention relates to the use of the above-defined test set of heterologous antisera, as well as a conventional agent for the enzyme activity determination in order to analyze an isoenzyme pattern of an enzyme in body fluids, extracts and/or excretions.

An isoenzyme pattern is generally understood to mean the sum total of the isoenzymes occurring in the individual organs, tissues, body fluids or excretions. More specifically, this term refers to the sum of diagnostically relevant isoenzymes of an enzyme occurring in multiple molecular forms.

Isoenzymes which cannot be determined immunologically are not to be covered by the term diagnostically relevant isoenzymes. Also, isoenzymes having a proportion of less than about 5% in the total activity of the enzyme are normally irrelevant diagnostically. However, there are several diagnostically relevant isoenzymes having a proportion of activity of less that 5%, for example the "Regan" isoenzyme of the alkaline phosphatase, which is tumor-specific in some cases; these are intended to chymotrypsin included within the scope of the present invention.

Suitable for the present invention are enzymes forming an isoenzyme pattern, i.e., occurring in multiple molecular forms, the isoenzymes of which a. are genetically differently determined and therefore have spatial orientation differences which can be immunologically detected;

b. exhibit a different distribution in the isoenzyme pattern in different organs and tissues or within one organ or tissue or within one cell; and c. can be precipitated practically quantitative by immunological methods — optionally with the use of auxiliary precipitants.

Illustrative diagnostically interesting enzymes include but are not limited to the oxidoreductases, e.g. the dehydrogenases such as glutamate dehydrogenase, glucose-6-phosphate dehydrogenase, lactate dehydrogenase, malate dehydrogenase and isocitrate dehydrogenase; transferases, such as the transaminases, e.g. glutamate oxalacetate transaminase [GOT] and glutamate pyruvate transaminase [GPT]; kinases, e.g. creatine kinase and hexokinase; phosphorylases, e.g. phosphorylase A and B; hydrolases, e.g. acidic and alkaline phosphatases; peptidases, e.g. leucine aminopeptidase, γ-glutamyl transpeptidase and alanine transpeptidase; proteases, e.g. trypsin, chymotryprin and pepsin; other hydrolases, e.g. amylase, neuraminidase and arginase; esterases, e.g. lipase, lipoprotein lipase, cholinesterase and microsomal esterases; nucleotidases, e.g. 5'-nucleotidase; lyases, e.g. aldolase; isomerases and ligases.

According to the present invention, preferred enzymes among those mentioned above are aldolase (ALD), creatine kinase (CK), lactate dehydrogenase (LDH), alkaline phosphatase (ALP), acidic phosphatase (AP), γ-glutamyl-transpeptidase (γ-GT), glutamate-oxalacetate-transaminase (GOT), glutamate pyruvate transaminase (GPT), hexokinase (HEX), and amylase, especially ALD, CK, LDH, ALP, γ-glutamyl transpeptidase, GOT and amylase.

The enzymes of particular diagnostic interest in accordance with this invention can be classified according to their distribution in organs and cells in correspondence with the following scheme:

1. Organ-specific isoenzymes wherein individual isoenzymes occur only in discrete organs, e.g. amylase isoenzyme in the parotid, pancreas and liver.

2. Enzymes occuring ubiquitously through the body, but the isoenzyme types of which gravitate to different organs with respect to the concentration, e.g., the characteristic isoenzyme pattern of alkaline phosphatase in bones, kidneys, the bile duct, liver, intestinal mucosa and placenta, acidic phosphatase in thrombocytes, the prostate, placenta and pancreas; aldolase in skeletal muscle, liver and brain; creatine kinase in skeletal muscle, brain and cardiac muscle (hybrids); hexokinase in the liver, skeletal muscle, brain and erythrocytes; γ-glutamyl transpeptidase in the liver, kidneys and pancreas; pyruvate kinase in erythrocytes, brain, cardiac muscle, skeletal muscle and kidneys, etc.

3. Enzymes occurring ubiquitously, the isoenzyme types of which are however distributed with respect to their frequency of occurrence among various cell organelles, e.g. in the cytoplasm, mitochondria, etc., e.g. GOT (aspartate aminotransferase) in the liver (cytoplasm 61%, mitochondria 39) and cardiac muscle; GPT (alanine aminotransferase) in the liver (cytoplasm 89%, mitochondria 11%), etc.

The distribution of many of the isoenzymes among individual organs, tissues, etc. is known from the literature, e.g. E. L. Coodley, "Diagnostic Enzymology," chapter 8, pp. 223–255, Philadelphia, Pennsylvania 1970; J. King, "Practical Clinical Enzymology," chapter 8, pp. 309–341, London 1965, J. H. Wilkinson, "Isoenzymes," London 1970.

Isoenzymes and their patterns can be determined according to the present invention in all parts of the body; however, preferred testing materials are biological fluids, body extracts and excretions. Biological fluids include but are not limited to extracellular body fluids such as whole blood, plasma, serum, bile, lymph, cerebrospinal fluid, intraocular fluid, pleural, pericardial, peritoneal, synovial and amniotic fluids. Extracts include but are not limited to intracellular tissue extracts such as extracts from blood corpuscles, liver, kidney, spleen, heart, lungs, testes, ovary, skin, spermatozoa, muscle, brain, bone, bone marrow, etc. Excretions include but are not limited to solids and liquids such as urine, stool, sputum and perspiration.

The isoenzymes employed as antigens can be obtained from various animals, especially from vertebrates, e.g. pigs, cattle, horses, sheep, goats, dogs, rabbits, monkeys, birds, guinea pigs, rats, mice. Among these animals, mammals such as pigs and cattle are preferred.

Suitable organ or tissue sources for the antigens include but are not limited to cardiac muscle, skeletal muscle, liver, gall bladder, pancreas, intestine, exocrine and endocrine glands, placenta, prostate, bones, cartilage, connective tissue, blood vessels, kidneys, spleen, lungs, brain, skin, spinal marrow and blood cells.

The isoenzyme antigens can be obtained from a living body by conventional techniques, e.g. by operation and/or biopsy. However, they are normally removed from a dead body; in contrast to the isoenzyme antigens derived from humans, the body parts containing the isoenzyme can be worked up directly after death, before autolysis occurs. This advantage is especially noticeable when the brain is worked up for this purpose.

The purity of the isoenzyme antigens is of great importance for the accuracy of the method of the present invention, since even minimum amounts of foreign antigen can excite the immune-competent cells to produce antibodies thereat. Therefore, the isoenzyme antigens employed must above all be free of the activities of the remaining isoenzymes. Absolute purity with respect to other, non-antigenic materials is of lesser significance.

A sensitive criterion for this purity requirement is immunological analysis which is advantageously conducted by means of diffusion or electrophoretic techniques. In addition, analytical disc electrophoresis and electrofocussing methods are useful.

Impurities can be separated by one or more suitable perparative methods. For example, in case of aldolase, either preparative electrofocussing in the pH range of between 7 and 10 and/or carrier-free preparative electrophoresis can be employed.

The isoenzyme antigens required for producing the antisera utilized in accordance with this invention should, in the ideal case, be extensively identical with the isoenzyme antigens to be tested, as a standard, especially with respect to their physical, enzymatic and immunological properties.

The isoenzyme antigen to be determined must, therefore, result in a maximally satisfactory cross-reaction with the heterologous antiserum. The limits of the method range at an approximately tenfold excess of the heterologous antiserum (compared with the required amounts of a homologous antiserum). An up to sixfold excess is preferred, especially a one- to fivefold excess.

The reason for this limitation is to be seen in that the precipitation optimum fixed by the Heidelberger curve, described in "Methods in Immunology and Immunochemistry III", edited by C. A. Williams and M. W. Chase, Academic Press New york, 1971, pages 1–58, is shifted in case of larger excesses of the antiserum to such an extent that the necessary, practically quantitative precipitation is no longer ensured. For example, aldolase A derived from pig muscle is suitable for the above-described method, since merely a 1.5-fold excess of the antiserum produced with the aid of this invention is required to also precipitate human aldolase practically quantitatively. In contrast thereto, the isoenzyme lactate dehydrogenase-$M_4$ (LDH-$M_4$) is unsuitable, because the human isoenzyme antigen is precipitated only with a 25-fold excess of the antiserum directed against pig skeletal muscle LDH-M$_4$, and even then no longer quantitatively.

The isoenzyme antigens to be determined must be at least 90%, preferably, 95–100% precipitable with the heterologous antiserum. In this way, the isoenzyme precipitated by the precipitin reaction can be practically completely removed from the analytical solution before the residual activity is determined. A removal of the precipitin complex is necessary, inter alia, because this complex can itself still possess a residual, although frequently only minor, enzyme activity.

The term practically complete precipitation as used herein refers to one which eliminates at least 90%, preferably 95–100% of the activity of a certain isoenzyme.

For the process of this invention, antisera are preferably employed from those animals which result in practically complete precipitations with the heterologous isoenzyne antigen to be precipitated. Suitable in this connection are primarily vertebrates, e.g. monkey types, horses, cattle, and bovine animals, goats, sheep, dogs, pigs (also the minipig), rabbits, gallinaceous birds, goose-type and duck-type birds, rats, guinea pigs, mice, etc. For obtaining larger amounts of antisera, sheep and/or horses or cattle are employed, e.g. for the production of precipitating antibodies against aldolase.

Frequently, the formation of practically entirely precipitating antisera depends, with a given type of animal, also on the particular breed of the individual animal selected for the immunization, and it is then advisable to screen representative breeds before undertaking a large-scale immunization program.

If practically complete precipitations cannot be effected with only the antisera employed, it is also possible to complete precipitation to the required degree with the aid of auxiliary precipitants known in immunology. Thus, it is possible, for example, to absorb the previously purified antiserum to suitable carriers and remove, with the aid of the thus-obtained reagents, a specific isoenzyme antigen from the test fluid.

Suitable carriers are known in the art and include but are not limited to latex particles which can be manufactured, e.g. from polystyrene, in any desired and exactly controllable size; erythrocytes treated with a tannin, e.g. m-digallic acid; glass; nitrocellulose; starch; ion exchange resins; parchment, etc.

It is also possible to obtain a complete precipitation by the use of "insoluble" antibody preparations. This is understood to mean the preferably covalent binding of the antibodies to an insoluble, generally polymeric carrier matrix. In principle, suitable carrier matrices for the covalent binding of antibodies are all natural or synthetic polymers to which suitable reactive groups can either be grafted or which already contain such groups. A survey of this technique is provided, for example, by E. Katchalski. I. H. Silman, and R. Goldman in F. F. Nord: "Advances in Enxymology," vol. 34, New York 1971, p. 445. Suitable carriers in this connection include but are not limited to highly substitued carboxymethylcellulose or cross-linked copolymers of ethylene and maleic anhydride. The binding of the antibodies to the carriers takes place, for example, according to the method described by W. Brummer et al., "Europ. J. Biochem," 25 (1972), p. 129, or in accordance with German Patent Application No. P 22 47 163.

Optionally, suitable insoluble antibodies can also be utilized as immune absorbents in a column, whereby it is possible to remove the individual isoenzymes chromatographically from the isoenzyme-containing test fluid. In yet another known procedure, the insoluble, antibody-containing immune absorbents are added to the test batch after first determining the total activity, the thus-produced insoluble antigen-antibody complex is separated by centrifuging or filtering, and the differential activity is determined in the supernatant.

Finally, it is also possible to precipitate those antigen-antibody complexes which precipitate only weakly or not at all by precipitating the entire $\gamma$-globulin complex with anti-$\gamma$-globulin sera. Since this method, as compared to the above-described procedures, requires an additional quantitative predetermination of the titer of total $\gamma$-globulins and furthermore since longer reaction times (e.g. 12 hours) must be expended, this method is presently less preferred for routine diagnostic operations.

The antisera are obtained according to processes generally known in immunology. There are described in detail, for example, in "Methods in Immunology and Immunochemistry," vol. 1, edited by C. A. Williams and M. W. Chase, Academic Press 1967. In order to elevate the antibody level of the immunized animal, it is also possible, inter alia, to utilize secondary immunization boosters. It is also possible to employ known adjuvants, e.g. Freund's adjuvant which represents a water-in-oil suspension optionally with the addition of killed mycobacteria.

The antibody titers of the resultant antisera can be determined with the aid of the above-mentioned Heidelberger curve which is obtained by titration of a specific amount by volume of antiserum with increasing amounts of isoenzyme antigen and by measuring the thus-produced turbidity values. The maximum of such a Heidelberger curve indicates the quantity of antiserum which completely precipitates a certain amount of antigen. Since the titer of the antisera varies, depending on the test animal and the type of immunization, it is advantageous to determine the antibody content of each individual antiserum or also a pool of several antisera, by means of immune titration with standardized isoenzyme antigen. The required antiserum excess can then also be readily ascertained from this titration.

The enzyme activity of the fluid to be tested is determined according to a standard method prior to and after the precipitation and removal of the antigen-antibody complex. A collection of standard methods for enzyme determination can be found, for example, in the handbook "Methoden der enzymatischen Analyse" [Methods of Enzymatic Analysis] 2nd edition, vol. 1, Weinheinm/Bergstrasse, 1970, edited by Hans Ulrich Bergmeyer. Standard methods of determining the enzyme activity in body fluids are furthermore described in "Empfehlungen der Deutchen Gesellschaft fuer Klinische Chemie" [Recommendations of the German Society for Clinical Chemistry] ("Z. Klin. Chemie und Klin. Biochemie" [Periodical of Clinical Chemistry and Clinical Biochemistry] 10 (1972), 182).

Among these standard methods, preferred are, for example, titrimetric methods, e.g. titration at a constant pH to determine lipase; photometric and turbidometric methods, e.g. those derived from spectralphotometric UV detection procedures or determinations in visible light; and manometric methods, e.g. those which can be conducted with a Warburg apparatus.

A practical illustration of the diagnostic analysis method will be further explained hereinbelow with reference to an isoenzyme determination in serum.

First of all, the total activity of the particular enzymes to be detected in the serum to be tested is determined in accordance with a conventional enzyme determination method. Thereafter, the serum specimen is divided into a number of aliquot samples corresponding to the diagnostically relevant isoenzymes. The aliquots are each combined with the heterologous antisera produced against the corresponding animal antigens. The quantity of antiserum to be added to each respective sample is dependent on the expected titer of the test sample and, as mentioned above, is determined with the aid of a preceeding Heidelberger curve titer determination of the antisera. Subsequently, a sodium chloride concentration favorable for the precipitation, which can range between 0.1 and 10%, but is ordinarily 0.5–5%, especially 2.5–4%, is set and then the mixture is incubated for 1minute to 5 hours, preferably 1–2 hours, at 10°–45°, but preferably at 25°–37°. Optionally, the mixture is allowed to stand for 10 minutes to 5 hours under refrigerator temperatures, e.g. at about 4° C. The resultant precipitate then is centrifuged at 1000–50,000 r.p.m., preferably about 5000–20,000 r.p.m. The centrifuging period fluctuates between ½ minute an 2 hours; however, the precipitate has ordinarily settled after about 10 minutes. Subsequently, a second enzyme determination is conducted in the supernatant to determine the residual enzyme activity. The difference with respect to the total activity therefore indicates the activity of the precipitated isoenzyme.

In the case of some of the enzymes to which the present determination method, can be applied, it is possible to completely detect the isoenzyme pattern of the fluid to be analyzed. However, in the case of other enzymes occurring in multiple molecular forms, the identity of all of the various isoenzyme types is not yet known or is scientifically disputed at the present state of the art. In such cases, it is sometimes impossible to determine all of the existing isoenzymes of the isoenzyme pattern. Some isoenzyme have only a relatively minor part in the total activity. e.g. a proportion of below 5%. In such cases, it is generally advantageous to determine diagnostically only those isoenzymes which occur with sufficient activity and are exactly determined, and to limit the data to these diagnostically relevant isoenzymes.

If an isoenzyme is organ- or tissue-specific, then a rise in serum isoenzyme activity can be disease-specific in case the respective organ or tissue is afflicted by a disease. In such a case, it is possible to restrict the analysis to the single, diagnostically relevant isoenzyme. However, normally the analysis must be effected for the determination of several diagnostically relevant isoenzymes.

A special problem is presented by the so-called "hybrid isoenzymes", which are formed by the combination of subunits of various isoenzymes in different proportions. Since the hybrids represent mixed forms between the individual pure isoenzyme types, they can also be precipitated to different extents by several antisera directed against the pure isoenzymes. Sometimes, enzyme activity values are simulated in this manner which are higher than the sum total of the isoenzyme activities which are actually present.

If the hybrids of a certain isoenzyme are ogran-specific, they increase the information content of the above-described immunological diagnostic method even further. This is the case, for example, with aldolase which occurs in a hybrid form only in cardiac muscle and in the brain. In such a case, a sum total of the isoenzyme activities which is determined substantially above 100% is a clear indication that the cardiac muscle or the brain is the originating organ. In numerous other enzymes, e.g. hexokinase, hybrids play a lesser part. Occassionally a reduction of the organ specificity can also occur, e.g. if hybrids exist regularly in several organs.

The above-described test method is not only suitable for larger institutions and/or clinics capable of producing immune sera, but is also usable, in the form of industrially manufactured test kits, by smaller institutions, hospitals and by the individual physician in his practice. A suitable test kit of this type can contain all of the reagents necessary to conduct the process of this invention, thus making it possible to accomplish the analysis with minimum expense. Such a mass-produced test kit contains, for example, antibodies and/or antisera (optionally each applied to a carrier and/or in covalent linkage with a carrier) against one, several or all diagnostically relevant isoenzymes of an enzyme occurring in multiple molecular forms, and furthermore a set of reagents adapted to practical use for the activity determination of the enzyme prior to and after precipitation.

The process of this invention, expecially the use of standardized test kits in accordance with this invention, now makes it possible to improve the organ-specific, tissue-specific, cell-specific, and/or disease-specific information content of enzyme diagnostics in a way not heretofore attainable. For example, it is now possible to determine quantitative data on the following problems, which heretofore could not be solved or could be solved in routine operations only qualitatively:

1. By a quantitative differentiation of the GOT isoenzymes, a distinction is made possible in some cases between the cytoplasmic and mitochrondria isoenzymes. This permits, for example, an indication of the degree of seriousness of cell damage.

2. The quantitative determination of the prostate-specific isoenzyme of acidic phosphatase can result in the recongnition of prostate afflictions such as prostate carcinoma at an earlier stage than heretofore possible.

3. The quantitative determination of the thrombocyte isoenzymes of acidic phosphatase can in certain cases improve the indication of danger of thrombosis in patients, e.g. in postoperative cases and during prolonged bed rest.

4. By the quantitative determination of the individual isoenzymes of alkaline phosphatase, the isoenzymes stemming from the bile duct epithelia can be differentiated quantitatively. This makes it possible to obtain data having a substantially greater informative value for the differential diagnosis of heptaobiliary diseases.

5. The quantitative determination of the individual isoenzymes of alkaline phosphatase makes it possible in some cases to differentiate quantitatively the isoenzyme stemming from the small intestine. These data can substantially facilitate the diagnosis of ileus.

6. A quantitative differentiation between the skeletal muscle isoenzyme and the cardiac muscle hybrids of creatine kinase is now possible, affording the possibility of an improved recognition of myocardiac infracts.

7. Isoenzymes of amylase stemming from the parotid and pancreas can in some cases be distinguished. Such data can substantially facilitate the diagnosis of pancreas diseases in certain circumstances.

Without further elaboration, it is believed that one skilled in the art, using the preceding description, utilize the present invention to its fullest extent. The following preferred specific embodiments are, therefore, to be construed as merely illustrative, and not limitative of the remainder of the specification and claims in any way whatsoever.

The temperatures herein are indicated in degrees Celsius.

EXAMPLE 1

Preparation of Anti-Aldolase A a. Isolation of Aldolase A from Pig Muscle 500 g. of pig skeletal muscle is comminuted with a meat grinder and combined under stirring with 2 liters of ice-cold 0.1M tris buffer, pH 7.5. 300 ml. portions are each homogenized with a mixer, and the homogenate is then centrifuged at 0° and at 13,000 g.'s. The effluent is saturated at 0° with solid ammonium sulfate up to a saturation of 0.3, i.e., to 30% saturation. After centrifuging the precipitate at 20,00 g.'s, the effluent is brought to a saturation of 0.65 s by the addition of further solid ammonium sulfate. After another centrifugation, the sediment is dissolved in 200 ml. of 0.01M tris buffer and dialyzed against the same buffer. The dialyzed tenate is applied to a phosphocellulose column (4 × 50 cm.) previously equilibrated with 0.01M tris buffer, pH 7.5. The column is washed free of protein. Other undesired proteins, e.g. hemoglobin, are removed by elution with 0.01M tris buffer. Finally, aldolase is eluted by means of 0.01M tris buffer containing 3 millimoles of frustose-1,6-diphosphate. By the addition of solid ammonium sulfate up to a saturation of 0.5 s, the enzyme is precipitated. After centrifuging, the aldolase A is dissolved in concentrated form in fresh buffer and crystallized by the gradual addition of solid ammonium sulfate to 0.5 s.

b. Preparation of Anti-Aldolase A

Sheep are used for immunization purposes. On three successive days, 5 mg. of enzyme dissolved in 2 ml. of 0.01M tris/HCl buffer, pH 8.0, and emulsified in the same volume of Freund's complete adjuvant, are injected intramuscularly. Thirty days after the last injection, a booster is given by the intravenous injection of 5 mg. of enzyme in 2 ml. of 0.9% NaCl. Ten days layer, 450 ml. of blood is withdrawn from the animals by puncturing the neck vein and, after the blood has coagulated, the serum is obtained by centrifugation (20 minutes, 3000 g.'s). The serum is stored in aliquots of 25 ml. at 12°.

From the Heidelberger curves it can be seen that, as compared to the homologous antiserum, 1.5 times as much of the heterologous antiserum is required to precipitate the aldolase A activity from human sera. The precipitation of the activity is 95% complete.

EXAMPLE 2

Preparation of Anti-Aldolase B a. Isolation of Aldolase B from Pig Kidneys

Analogously to the work of O. Alarcon, F. Gonzalez, H. Flores, and F. Marcus, reported in Biochim. Biophys. Acta 227:460 (1971), the enzyme is isolated from pig kidneys. 500 g. of pig kidneys from freshly slaughtered pigs is finely ground in a meat grinder and homogenized for 3 minutes in an "Ultra-Tarrax" mixer in 2 volumes of 10 millimoles of mercaptoethanol and 1 millimole of EDTA (pH 7.5) cooled to 2°. After centrifugation for 60 minutes at 20,000 g.'s, the ph of the extract is lowered to pH 4.0 by the addition of 2N acetic acid. The mixture is centrifuged for 20 minutes at 12,000 g.'s and after 5 minutes, the pH of the effluent is adjusted to pH 7.5 with 2M tris solution. The thus-produced precipitate is separated by centrifuging, and the effluent is subjected to a fractional ammonium sulfate precipitation. The protein fraction precipitated between 0.52 s and 0.65 s is taken up in 10 ml. or 0.05M tris/CHl (10 millimoles of mercaptoethanol, 1 millimole of EDTA), pH 8.0, and freed from ammonium sulfate by dialysis against the same buffer. The tanate protein fraction is applied to a phosphocellulose column (2.5 × 25 cm.) equilibrated with the same buffer. After washing the column protein-free with this buffer, aldolase B is eluted by adding 0.1M NaCl to the elution buffer. The enzymatically active fractions are combined and saturated to 0.8 s with ammonium sulfate. The precipitated enzyme is washed with a 0.55 s ammonium sulfate solution, finally taken up in 3 ml. of 0.05M tris/HCl (10 millimoles of mercaptoethanol, 1 millimole of EDTA), and stored as a suspension in 0.7 s ammonium sulfate at 40°.

b. Preparation of Anti-Aldolase B

Sheep are utilized for immunization purposes. The immunization is conducted analogously to Example 1(b). A comparison of the Heidelberger curves shows that, for the precipitation of aldolase B from human sera, 2.8 times the amount of the heterologous antiserum, as compared to the homologous antiserum, is necessary. 96% of the aldolase B activity is precipitated.

EXAMPLE 3

Distribution of the Aldolase Isoenzymes in Human Organ Extracts and Body Fluids

In accordance with the process described in the referenced copending U.S. patent application, the total activity of the aldolase is determined in extracts of human organs and in human sera. For the determination of aldolase activities in biological fluids, 2.5 ml. of a solution consisting of 4 millimols of fructose-1,6-diphosphate, 0.3 millimol of iodacetate (sodium salt of moniodoacetic acid), and 55 millimols of collidine buffer (0.55 millimols of collidine, adjusted to a pH of 7.4 with hydrochloric acid) is mixed with 0.05 ml. of a 15mM $\beta$-nicotinamide adenine dinucleotide solution and 0.01 ml. of a suspension consisting of 0.28 U/ml of glycerin 3-phosphate dehydrogenase, 1.7 U/ml. of triose phosphate isomerase and 0.65 U/l. of lactate dehydrogenase in 2.8M ammonium sulfate solution. To this mixture is added 0.20 ml. of the serum to be tested, the solution is mixed and maintained at +37° for 5 minutes. The extinction coefficient $E_1$ is measured against a blank value, and the mixture allowed to stand for exactly 20 minutes. Thereupon, the extinction coefficient $E_2$ is measured against a blank value containing only 0.20 ml. of the serum to be examined and 2.5 ml. of 0.9% sodium chloride solution.

The aldolase content is calculated in accordance with the following formula:

$$\text{Volume Activity} = \frac{1000 \cdot V}{\epsilon \cdot d} (E_1 - E_2) / (t_2 - t_1) \, mU/ml.$$

wherein:
V = test volume
$\epsilon$ = extinction coefficient (cm$^2$/μmol)
d = layer thickness (cm)
$(t_2-t_1)$ = measuring time interval (minutes)

For the determination of aldolase isoenzymes in raw extracts of human organs, one millimeter of a human tissue raw extract is mixed with 1 ml. of an anti-A (anti-aldolase-A) serum, and the final concentration of sodium chloride is adjusted to 4%. The mixture is incubated at 37° for 60 minutes and then stored for 2 hours at +40°. After centrifuging off the immune precipitate at 20,000 g., the aldolase activity of the supernatant is determined in accordance with the above method. Analogously, with 1 ml. of anti-b or anti-C, the aldolase B and aldolase C, respectively, are precipitated from other 1 ml. portions of the same tissue raw extract and the remaining residual aldolase activity in the supernatant is determined.

Thereafter, the test specimens are divided into two equal portions and, according to the above-described method, aldolase A is precipitated in one sample with anti-aldolase A and aldolase B is precipitated with anti-aldolase B in the other sample. The antisera employed are preparations obtained by immunization of test animals with animal antigens. After separation of the antigen-antibody precipitates, the aldolase activity which has not been precipitated is determined in both specimens.

The following table summarizes the percentage proportions of aldolases A and B measured in the organ extracts and sera. Since the proportion of aldolase C has not been determined, the arithmetical difference of the sum of aldolase A + aldolase B with respect to the measured total activity is called "residual activity", i.e., the activity attributable to aldolase C and hybrids. Due to the cross-reaction with hybrids, the sum total of the activities of aldolases A + B + C can be above 100%.

| Tissue | Percentage Proportions of Aldolase A | Residual Aldolase B | Activity |
|---|---|---|---|
| Organ extracts | | | |
| Skeletal muscle | 95 | 1 | 4 |
| Cardiac muscle | 87 | 8 | 5 |
| Brain | 76 | 1 | 23 |
| Kidney | 25 | 70 | 5 |
| Liver | 3 | 99 | — |
| Sera | | | |
| Normal 1 | 83 | 17 | 0 |
| Viral hepatitis | 8 | 94 | — |
| Cardiac infarct | 71 | 21 | 8 |

EXAMPLE 4

Preparation and Utilization of the Antiserum Against Creatine Kinase MM from Pig Muscle a. Isolation of Creatine Kinase MM from Pig Muscle 500 g. of pig muscle is ground in a meat grinder, suspended in 2 liters of ice-cold 0.05M tris/HCl buffer (0.01M KCl, 1 millimole of EDTA, 1 millimole of mercaptoethanol), pH 8.0, and homogenized by means of an "Ultra-turrax" mixer for 3 minutes at 0°-2°. The homogenate is centrifuged in a cooled centrifuge at 0°-2° and 13,000 g.'s, and the clear supernatant is saturated to 0.4 s with solid ammonium sulfate. The thus-obtained precipitate is separated by centrifugation, and the ammonium sulfate concentration is increased to 0.75 by adding solid amonium sulfate. The resultant precipitate is taken up in concentrated form in tris/HCl buffer (10 millimoles of mercaptoethanol, 1 millimole of EDTA), pH 8.0, and dialyzed against the same buffer at 5° for 18 hours. The tenate is applied to a column (6 × 60 cm.) of weakly basic ion exchanger previously equilibrated with 0.1M tris/HCl buffer (1 millimole of mercaptoethanol, 1 millimole of EDTA), pH 8.0. After washing the column thoroughly with the same buffer, the enzyme is eluted by applying a linear NaCl gradient (up to 0.1M, NaCl); the active fractions are combined and saturated to 0.4 s with solid ammonium sulfate. After the separation of an initial minor precipitate, the ammonium sulfate concentration is increased to 0.75 s, the precipitated enzyme is dissolved in concentrated form in the above buffer, and filtered over a column (2.5 × 90 cm.) of a weakly basic ion exchanger. The fractions having a specific activity of 20–25 U/mg. are combined, and the isoenzyme is stored as a suspension in 0.7 s ammonium sulfate at 5°.

b. Preparation of the Antiserum Against Creatine Kinase MM Rabbits are utilized for immunization purposes.

Immunization scheme: Primary injection, intramuscular, 5 mg. of CK-MM, dissolved in 1 ml. of 0.01M tris/HCl buffer, pH 8.0, and emulsified in the same volume of complete Freund's adjuvant (FA). After 10 days, 5 × 0.1 ml. of this antigen emulsion is injected intradermally at five different locations in the skin of the back. Boosting is effected after 32 days by intramuscular injection of 2 mg. of antigen. After another 8 days, about 100 ml. of blood is withdrawn from the rabbits by ear vein puncture, the serum is collected and stored at a constant temperature of 12°.

The antibody titers of the aldolase antisera are determined as described in the referenced U.S. Patent Application.

This determination is conducted with the aid of a "Heidelberger" curve. Constant amounts of the antisera are mixed with increasing quantities of one of the homologous antigens/aldolase A, B and C, and solid sodium chloride is added to a final concentration of 4%. After incubation of one hour at 37° and a storage time of 2 hours in a refrigerator, the turbidities produced by immune precipitation are measured in a spectrophotometer at 436 nanometers using a 1 cm.-cuvette against a blank value. After removing the immune precipitate by centrifugation, the activity of the residual non-precipitated aldolase can be measured in the clear supernatant.

After a Heidelberger curve has been prepared, it can be seen that, as compared to the homologous antisera, four times the amount of heterologous antiserum is required to completely precipitate the CK isoenzyme MM from human sera.

c. Proportion of Creatine Kinase MM in the Total Activity of CK in Human Organs

With the aid of a determination of the CK total activity and the determination of the CK activity after precipitation with CK-MM antiserum, the following proportion of the isoenzyme MM in the CK activity was measured in various organs:

| Organ | CK Activity of the Extract (U/l.) | Proportion Isoenzyme MM (%) |
|---|---|---|
| Skeletal muscle | 820 | 82 |
| Heart | 1120 | 65 |
| Brain | 500 | 5 |

EXAMPLE 5

Test Kit for the Immunological Determination of the Activity of the Creatine Kinase isoenzyme MM in Body Fluids 1. Composition of the Test Kit a. 50 ml. of ready-for-use buffered substrate solution, pH 7.0, containing the following components:

| | | |
|---|---|---|
| Triethanolamine | 105 | millimoles |
| Glucose | 21 | millimoles |
| Magnesium acetate | 10.5 | millimoles | b. Twenty bottles of lyophilized reagent mixture sufficient for one analysis per two bottles. Each bottle contains the following components:

| | | |
|---|---|---|
| Creatine phosphate | 73.5 | $\mu$mol |
| Reduced glutathione | 18.9 | $\mu$mol |
| Adenosine diphosphate | 2.1 | $\mu$mol |
| Nicotinamide adenine dinucleotide phosphate | 1.26 | $\mu$mol |
| Adenosine monophosphate | 21.0 | $\mu$mol |
| Hexokinase, at least | 2.5 | U |
| Glucose-6-phosphate dehydrogenase, at least | 2.5 | U | c. One bottle of antiserum
Titer: 1000 mU CK-MM/ml
Final concentration NaCl = 5%

2. Conductance of the analysis a. Immune Precipitation: mix 0.5 ml. of human serum + 0.5 ml. of antiserum, incubate for 1 hour at 37°, then for one hour at 4°, centrifuge 10 minutes at 10,000 r.p.m.

b. Activity Measurement
The following volumes are employed:
(for total activity:
  2.0 ml. of buffered substrate solution
  0.1 ml. of test serum
($\beta$) for residual activity after precipitation:
  2.0 ml. of buffered substrate solution
  0.1 ml. of supernatant from precipitation Mix the reagent and incubate for 5 minutes at 25°, then pour into a cuvette (layer thickness 1 cm.) and observe the change in extinction coefficients at 25° for 5 minutes at a wavelength of 366 nm.

c. Calculation

The change in extinction coefficient per minute $\Delta E_{total/min.}$ and $\Delta D_{prec./min.}$, respectively, is determined for both the total analysis and the analysis after precipitation. Isoenzyme activity = $(\Delta D_{total/min.} - 2\Delta E_{prec./min.}) \cdot 6364$ U/l.

EXAMPLE 6

Use of Carrier-Bound Anti-Aldolase A for Immune Precipitation a. Enrichment of the Immune Globulins in the Antiserum A γ-globulin fraction is obtained in the pure form from the heterologous anti-A sheep serum produced according to the directions of Example 1(a), with a titer of 120 mU/ml., by precipitation with saturated ammonium sulfate solution (up to a saturation of 0.33 s, pH 6.5) and subsequent chromatography on weakly basic, cellulose-containing ion exchanger according to Y. L. Fahey and E. W. Terry, "Handbook of Experimental Immunology" edited by D. M. Weir, Oxford, 1967, p. 19. From 100 ml. of sheep serum, 420 ml. of γ-globulin solution is obtained in 0.9% of NaCl (0.01M phosphate, pH 8.0) with a protein content of 28 mg./ml.

b. Binding of the Immune Globulins to Carriers

One gram of carboxymethylcellulose hydrazide (3.0 meq./g. of acid hydrazide groups) is dissolved in 80 ml. of $H_2O$, mixed with 0.3 ml. of 25% aqueous glutaric dialdehyde, and the thus-formed gel is homogenously suspended. The suspension is cooled to 0°; the pH is lowered to 1.2 by adding 5N HCl, and the mixture is combined with 5.2 ml. of 5% $NaNO_2$ solution. After 5 minutes, the gel is vacuum-filtered, washed with distilled water, and immediately made into a homogeneous suspension with a solution, cooled to 2°, of 10 ml. of immune globulin concentrate in 40 ml. of 0.2M tris/HCl buffer, pH 8.0. After one hour, unbound antibody protein is removed by sequentially washing the gel with 1 liter of 0.2M tris/HCl buffer (0.5M NaCl), pH 8.5; 0.2M acetate buffer (0.5M NaCl), pH 4.5; 0.2M $K_2HPO_4$; and finally distilled $H_2O$; the gel is then lyophilized, yielding 960 mg. of lyophilized substance having a protein content of 160 mg./g. The protein content is determined from the difference between the amount utilized and the residual quantity which has remained in the reaction solution and in the reaction solution and in the washing solutions. 86% of the immunological activity of the bound antibody protein has been preserved.

c. Investigation of a Pathological Serum 1 ml. of serum from a patient suffering from muscular dystrophy, having a total aldolase activity of 49 mU/ml., is combined with 50 mg. of the carrier-bound anti A-serum and circulated in a rotary mixer for 30 minutes at room temperature. The thus-formed insoluble antigen/antibody complex is separated by means of a table centrifuge (2 minutes, 10,000 g.'s), and the aldolase activity is determined in the effluent according to the method described in Bergmeyer, "Handbuch der enzymatischen Analyse" [Handbook of Enzymatic Analysis], Weinheim/Bergstrasse, 2nd edition 1970, p. 1062. The proportion of aldolase A in the patient's serum is 97%.

The preceding examples can be repeated with similar success by substituting the generically and specifically described reactants and operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A process for the quantitative determination of at least one diagnostically relevant isoenzyme form of a human enzyme occuring in a plurality of genetically defined, immunologically differentiable multiple isoenzyme forms, which comprises:
   a. quantitatively measuring the total enzyme activity of said multiple isoenzyme forms in a human body fluid, tissue extract or excretion sample;
   b. admixing a portion of said sample with a one to tenfold theoretical excess, based on the amount of antisera to the human isoenzyme antigens required to precipitate at least 90% of said antigens, of a precipitating antibody against an isoenzyme group of a heterologous species corresponding to a diagnostically relevant isoenzyme form, which antibody is substantially free of immunological activity against other of said multiple isoenzyme forms, to produce a substantially quantitative antigen-antibody immunoprecipitin complex consisting essentially of said diagnostically relevant human isoenzyme form and said antibody;
   c. substantially quantitatively separating said immunoprecipitin complex from the resultant admixture so that at least 90% of the diagnostically relevant human isoenzyme form activity is removed therefrom; and
   d. quantitatively measuring the total enzyme activity of the remaining multiple isoenzyme forms substantially free of the diagnostically relevant human isoenzyme form, whereby the diagnostically relevant human isoenzyme form can be quantitatively determined.

2. A process according to claim 1 wherein said precipitation is further aided by an auxiliary non-immunological precipitant.

3. A process according to claim 2 wherein said auxiliary precipitant is a carrier on which said antiserum is fixed.

4. A process according to claim 1 wherein the isoenzyme antigen which is precipitated is a single diagnostically relevant isoenzyme.

5. A process according to claim 1 wherein at least one isoenzyme of said isoenzyme group is a hybrid isoenzyme.

6. A process according to claim 1 wherein said isoenzymes are those of an enzyme selected from the group consisting of aldolase, creatine kinase, lactate dehydrogenase, alkaline phosphatase, acidic phosphatase, γ-glutamyl transpeptidase, glutamate oxalacetate transaminase, glutamate pyruvate transaminase, hexokinase and amylase.

7. A process according to claim 6, wherein said enzyme is aldolase.

8. A process according to claim 6, wherein said enzyme is creatine kinase.

9. A process according to claim 6, wherein said enzyme is alkaline phosphatase.

10. A process according to claim 6, wherein said enzyme is acid phosphatase.

11. A process according to claim 6, wherein said enzyme is lactate dehydrogenase.

12. A process according to claim 1, wherein the reagents employed consist essentially of:
   a. A test set of individual heterologous immunoprecipitating antisera directed against the corresponding individual diagnostically relevant isoenzymes of the isoenzyme pattern to be tested, which antisera are each substantially free of immunological activity against other of said isoenzyme forms, respectively precipitable to an extent of at least 90% with the isoenzyme antigens to be determined, and which antisera each result in a practically quantitative immunoprecipitin cross-reaction at a one- to tenfold excess, based on the homologous antiserum; and
   b. an isoenzyme substrate agent for determining enzyme activity of said isoenzyme prior to and after precipitation.

* * * * *